US010739243B2

(12) United States Patent
Su et al.

(10) Patent No.: US 10,739,243 B2
(45) Date of Patent: Aug. 11, 2020

(54) INTEGRATED MONITORING SYSTEM AND MONITORING METHOD FOR SEEPAGE BEHAVIOR OF WATER ENGINEERING IN COMPLEX ENVIRONMENT

(71) Applicant: HOHAI UNIVERSITY, Jiangsu (CN)

(72) Inventors: Huaizhi Su, Jiangsu (CN); Chongshi Gu, Jiangsu (CN); Meng Yang, Jiangsu (CN)

(73) Assignee: HOHAI UNIVERSITY, Jiangsu (CN)

( * ) Notice: Subject to any disclaimer, the term of this patent is extended or adjusted under 35 U.S.C. 154(b) by 159 days.

(21) Appl. No.: 16/300,046

(22) PCT Filed: Dec. 30, 2016

(86) PCT No.: PCT/CN2016/108629
§ 371 (c)(1),
(2) Date: Nov. 8, 2018

(87) PCT Pub. No.: WO2017/193570
PCT Pub. Date: Nov. 16, 2017

(65) Prior Publication Data
US 2019/0145880 A1 May 16, 2019

(30) Foreign Application Priority Data
May 10, 2016 (CN) .......................... 2016 1 0305522

(51) Int. Cl.
*G01N 15/08* (2006.01)
*G02B 6/02* (2006.01)
*G01N 33/24* (2006.01)

(52) U.S. Cl.
CPC ......... *G01N 15/0806* (2013.01); *G01N 15/08* (2013.01); *G01N 33/24* (2013.01); *G02B 6/02* (2013.01); *G01N 2015/0846* (2013.01)

(58) Field of Classification Search
CPC .... G01N 15/0806; G01N 15/08; G01N 33/24; G01N 2015/0846; G02B 6/02
See application file for complete search history.

(56) References Cited

U.S. PATENT DOCUMENTS 5,399,854 A * 3/1995 Dunphy .................... G01K 5/72
250/227.17
5,567,932 A * 10/1996 Staller ..................... G01M 3/38
250/227.14

(Continued)

FOREIGN PATENT DOCUMENTS

| CN | 1920178 | 2/2007 |
|---|---|---|
| CN | 101799430 | 8/2010 |

(Continued)

OTHER PUBLICATIONS

"International Search Report (Form PCT/ISA/210)", dated Mar. 1, 2017, with English translation thereof, pp. 1-6.

*Primary Examiner* — David A. Rogers
(74) *Attorney, Agent, or Firm* — JCIPRNET

(57) ABSTRACT

The present invention discloses an integrated monitoring system and monitoring method for a seepage behavior of water engineering in a complex environment, the system includes a seepage character space-time monitoring device and a sensing fiber seepage-monitoring sensitizing device, the seepage character space-time monitoring device includes a vertical force-bearing fiber-carrying column, an outer edge through pipe and a sensing fiber, a left force-bearing beam and a right force-bearing beam are disposed at two sides of the vertical force-bearing fiber-carrying column respectively, the outer edge through pipe is sleeved over the vertical force-bearing fiber-carrying column, a fiber collecting box is disposed above a second transitional round end, the sensing fiber in the fiber collecting box runs through the outer edge through pipe to be connected to a component (Continued)

supporting body containing a temperature measuring device, and then runs through an elastic device after sequentially bypassing the second transitional round end and a first transitional round end to be led out from a third transitional round end. The integrated monitoring system for a seepage behavior of water engineering in a complex environment, with a series of products and technologies such as research and development in basic sensing fibers and secondary processing of common sensing fibers being provided, implements quantitative and qualitative assessments in the horizontal and longitudinal directions in terms of time and space.

8 Claims, 7 Drawing Sheets

(56) References Cited

U.S. PATENT DOCUMENTS

| | | | | |
|---|---|---|---|---|
| 5,663,490 | A * | 9/1997 | Kozen | G01M 3/002 405/54 |
| 6,097,486 | A * | 8/2000 | Vakoc | G01D 5/35383 356/477 |
| 6,648,552 | B1 * | 11/2003 | Smith | B09B 1/00 405/129.5 |
| 7,141,815 | B2 * | 11/2006 | Yankielun | G01D 5/35338 250/577 |
| 7,777,496 | B2 * | 8/2010 | Evans | G01N 21/84 324/534 |
| 8,199,317 | B2 * | 6/2012 | Habel | E02B 3/10 356/32 |
| 8,316,694 | B2 * | 11/2012 | Artieres | G01M 3/047 73/40 |
| 9,140,582 | B2 * | 9/2015 | Farhadiroushan | E21B 47/002 |
| 9,541,425 | B2 * | 1/2017 | Farhadiroushan | G01D 5/35358 |
| 9,804,021 | B2 * | 10/2017 | Farhadiroushan | E21B 47/002 |
| 10,393,572 | B2 * | 8/2019 | Farhadiroushan | G01F 1/66 |
| 10,393,573 | B2 * | 8/2019 | Farhadiroushan | G01D 5/35383 |
| 10,393,574 | B2 * | 8/2019 | Farhadiroushan | E21B 47/002 |
| 2003/0127587 | A1 * | 7/2003 | Udd | G01L 1/246 250/227.14 |
| 2005/0077455 | A1 * | 4/2005 | Townley-Smith | G08B 13/124 250/227.27 |
| 2008/0084914 | A1 * | 4/2008 | Yamamoto | G01B 11/18 374/137 |
| 2009/0303460 | A1 * | 12/2009 | Habel | G01M 11/086 356/32 |
| 2010/0013497 | A1 * | 1/2010 | Evans | G01N 21/84 324/642 |
| 2013/0319121 | A1 * | 12/2013 | Hill | G01H 9/004 73/645 |
| 2014/0025319 | A1 * | 1/2014 | Farhadiroushan | E21B 47/095 702/56 |

FOREIGN PATENT DOCUMENTS

| | | |
|---|---|---|
| CN | 101963493 | 2/2011 |
| CN | 203204213 | 9/2013 |
| CN | 204789002 | 11/2015 |
| CN | 105738268 | 7/2016 |
| JP | 2001082934 | 3/2001 |
| JP | 2001311127 | 11/2001 |

* cited by examiner

INTEGRATED MONITORING SYSTEM AND MONITORING METHOD FOR SEEPAGE BEHAVIOR OF WATER ENGINEERING IN COMPLEX ENVIRONMENT

CROSS-REFERENCE TO RELATED APPLICATION

This application is a 371 application of the international PCT application serial no. PCT/CN2016/108629, filed on Dec. 30, 2016, which claims the priority benefit of China application no. 201610305522.1, filed on May 10, 2016. The entirety of each of the abovementioned patent applications is hereby incorporated by reference herein and made a part of this specification.

BACKGROUND

Technical Field

The present invention relates to an integrated monitoring system and monitoring method for a seepage behavior of water engineering in a complex environment, and belongs to the field of water engineering health monitoring.

Background Art

Water engineering is a systematic project with a large scale, a complex structure and a variable external load. Traditional research is mostly based on the development of classical theories of mathematics and mechanics. The safety characteristics of dike structures are analyzed from a qualitative and static perspective. The influence of the variability and dynamics of internal parameters on long-term effects of an engineering structure itself is ignored. Penetration damage is one of the most important factors affecting the safety of hydraulic structures. In order to control the seepage behavior of hydraulic structures in time, it is necessary to arrange various types of sensor devices inside the structures. A traditional sensing device often has the problems of influence on a monitoring effect such as poor anti-electromagnetic interference capability, susceptibility to a humid environment, short service life, single-point single physical quantity monitoring, too many leads, and large proneness to measurement drift. Therefore, it is necessary to develop advanced and practical monitoring technologies and equipment. With the continuous improvement of people's safety awareness and monitoring technologies, a number of representative methods have been derived: ultrasonic testing methods, acoustic methods, magnetic powder methods, ground penetrating radar, tracer methods and the like, but this new method has little effect on seepage monitoring of water engineering. It is necessary to improve an old technology and explore a new technology. A distributed fiber monitoring technology is a relatively mature monitoring means, which has strong anti-electromagnetic interference capability, is not susceptible to an external environment, has a long service life, can realize distributed multi-parameter monitoring, is not prone to measurement drift, and has the advantages of low price, convenient layout, etc. Therefore, in view of that the application research of a sensing fiber technology in water engineering is of great significance, but the distributed fiber monitoring technology has poor practicability in the field of seepage monitoring of water engineering, it cannot be directly applied to the field of seepage monitoring of water engineering, and needs to be improved and innovated. A sensing system for seepage monitoring based on a distributed fiber technology which may be truly practical is proposed and created.

SUMMARY OF THE INVENTION

Objective of the Invention

In order to overcome the deficiencies in the prior art, the present invention provides an integrated monitoring system and monitoring method for a seepage behavior of water engineering in a complex environment, which has the characteristics of convenient layout, distributed monitoring, synchronous operation, flow, and high efficiency, has the advantages of low cost, simple operation and excellent effect, and can realize automatic information collection of a full time domain structure to be monitored. A serialized and integrated monitoring technology has the outstanding advantages of reducing the monitoring cost, improving the monitoring precision and improving the engineering practical ability.

Technical Solution

In order to achieve the above objective, an integrated monitoring system for a seepage behavior of water engineering in a complex environment of the present invention includes a seepage character space-time monitoring device and a sensing fiber seepage-monitoring sensitizing device.

The seepage character space-time monitoring device includes a vertical force-bearing fiber-carrying column, an outer edge through pipe and a sensing fiber, a left force-bearing beam and a right force-bearing beam are disposed at two sides of the vertical force-bearing fiber-carrying column respectively, the outer edge through pipe is sleeved over the vertical force-bearing fiber-carrying column, the top end of the vertical force-bearing fiber-carrying column is provided with a second transitional round end, the bottom end is provided with a component supporting body, a first transitional round end and a third transitional round end are disposed at both ends of each of the left force-bearing beam and the right force-bearing beam respectively, elastic devices are disposed below the left force-bearing beam and the right force-bearing beam respectively, a fiber collecting box is disposed above the second transitional round end, and the sensing fiber in the fiber collecting box runs through the outer edge through pipe to be connected to the component supporting body containing a temperature measuring device, is disposed in the vertical force-bearing fiber-carrying column in an S shape, and then runs through the elastic devices below the left force-bearing beam and the right force-bearing beam after sequentially bypassing the second transitional round end and the first transitional round end to be led out from the third transitional round end.

The sensing fiber seepage-monitoring sensitizing device includes a central control module, outer layer modules and port modules, the outer layer modules and the port modules are disposed at both sides of the central control module, and the outer layer modules are located between the central control module and the port modules.

The central control module includes a through pipe handle, an upper through pipe, a glue injection through pipe and a lower through pipe, one end of the through pipe handle is connected to the glue injection through pipe, the glue injection through pipe is embedded between the upper through pipe and the lower through pipe, and the sensing fiber is located between the upper through pipe and the lower through pipe.

The outer layer module includes an inner super hard layer, an inner heat insulation layer, an outer heat transfer layer, an inner heat conduction enhancement layer, an outer hard layer, and an outer temperature insulation enhancement layer, the inner side of the inner super hard layer is connected to the outer side of the inner heat insulation layer, the inner super hard layer is adjacent to the inner heat conduction enhancement layer, the outer side of the inner heat conduction enhancement layer is connected to the inner layer of the outer heat transfer layer, the inner heat conduction enhancement layer is adjacent to the outer temperature insulation enhancement layer, the outer side of the outer temperature insulation enhancement layer is connected to the inner side of the outer hard layer, the outer temperature insulation enhancement layer is adjacent to a solid fiber end, and the sensing fiber sequentially runs through the inner heat insulation layer, the inner heat conduction enhancement layer and the outer temperature insulation enhancement layer.

The port module includes an upper glue injection pipe, a spherical solid fiber end, a solid storage pipe and a lower glue injection pipe, the upper glue injection pipe is fixed to the upper end side of the solid fiber end, the solid storage pipe is fixed at a middle position of the solid fiber end, the lower glue injection pipe is fixed to the lower end side of the solid fiber end, and the sensing fiber passes through the solid storage pipe.

Preferably, the sensing fiber is a seepage behavior monitoring sensing cable, and includes an outer circle module, a middle layer module and an inner core module, the middle layer module being located between the outer circle module and the inner core module.

The inner core module includes a fourth sensing fiber and an inner triangular support, the fourth sensing fiber is wrapped with a hard protective layer, a heat insulation protective layer is disposed outside the hard protective layer, the inner triangular support is disposed outside the heat insulation protective layer, and the fourth sensing fiber is located at the center of the inner triangular support.

The middle layer module includes a first sensing fiber, a second sensing fiber, a third sensing fiber and an outer arc filling layer, the first sensing fiber, the second sensing fiber and the third sensing fiber are located between the inner triangular support and the outer circle module, and the outer arc filling layer is arranged between the inner triangular support and the outer circle module for fixing the first sensing fiber, the second sensing fiber and the third sensing fiber.

The outer circle module is annular, and includes not less than two sets of seepage isolating enhancement segments and seepage enhancing reinforcement segments, the seepage isolating enhancement segments and the seepage enhancing reinforcement segments are alternately distributed, and the seepage isolating enhancement segments and the seepage enhancing reinforcement segments wrap the first sensing fiber, the second sensing fiber and the third sensing fiber.

Preferably, the elastic device includes a first elastic expansion member and a plurality of second elastic expansion members distributed side by side; the first elastic expansion member includes a first elastic pipe, a first expansion spring, a first fiber-carrying connecting shaft, and a first fiber-carrying ring connected to the first fiber-carrying connecting shaft, the first expansion spring being located in the first elastic pipe, and the first fiber-carrying connecting shaft being connected to the first expansion spring; and the second elastic expansion member includes a second elastic pipe, a second expansion spring, a second fiber-carrying connecting shaft, and a second fiber-carrying ring connected to the second fiber-carrying connecting shaft, the second expansion spring being located in the second elastic pipe, the second fiber-carrying connecting shaft being connected to the second expansion spring, and the sensing fiber sequentially running through the first fiber-carrying ring and the second fiber-carrying ring.

Preferably, there are four second elastic expansion members, the sensing fiber sequentially runs through the first fiber-carrying ring below the left force-bearing beam, four second fiber-carrying rings below the left force-bearing beam, four second fiber-carrying rings below the right force-bearing beam, and the first fiber-carrying ring below the right force-bearing beam, and the sensing fiber is distributed in an S shape.

Preferably, two sides of the central control module are symmetrically provided with an outer layer module and a port module, an end portion of the solid storage pipe is provided with a transitional wheel, and the sensing fiber is connected to a weight-increasing vertical pull block after bypassing the transitional wheel.

Preferably, the hard protective layer includes three inner hard four-sided layers, the inner hard four-sided layer is of a parallelogram with an interior angle of 60°, the fourth sensing fiber is located at the center of the intersection of the three inner hard four-sided layers, and the inner triangular support is of an equilateral triangle.

Preferably, the heat insulation protective layer includes three sets of anti-seepage triangular layers and heat-insulating triangular layers, each set of anti-seepage triangular layer and heat-insulating triangular layer is located at one corner of the inner triangular support, each set of anti-seepage triangular layer and heat-insulating triangular layer is symmetrically distributed about an angle bisector of the inner triangular support, and the anti-seepage triangular layer and the heat-insulating triangular layer are seamlessly connected to the inner hard four-sided layer.

A monitoring method of the foregoing integrated monitoring system for a seepage behavior of water engineering in a complex environment includes the following steps:

first, preparing a common sensing fiber based on actual engineering monitoring needs, determining a length of the sensing fiber to be sensitized, fixing a weight-increasing vertical pull block to a head end of a segment to be sensitized in the sensing fiber, fixing another weight-increasing vertical pull block to a tail end, injecting glue into a solid storage pipe through an upper glue injection pipe and a lower glue injection pipe in a solid fiber end, opening through pipe handles at upper and lower ends to make the glue flow out from glue injection through pipes at upper and lower sides simultaneously, and continuously squeezing the glue to positions, in contact with the sensing fiber, in an inner heat insulation layer, an inner heat conduction enhancement layer and an outer temperature insulation enhancement layer at both sides, so that the inner heat insulation layer, the inner heat conduction enhancement layer and the outer temperature insulation enhancement layer are closely engaged with the sensing fiber, and the sensing fiber at the glue injection through pipe is encapsulated and sealed together by glue;

second, providing four common sensing fibers with the same length and factory parameters and different colors of tight sheathing layers, sequentially constructing an outer circle module, a middle layer module and an inner core module, then sequentially assembling the inner core module, the middle layer module and the outer circle module in an order from the inside to the outside, recording the colors and corresponding directions of the tight sheathing layers outside the common sensing fibers in different directions, heating an inner triangular support, stopping heating after the temperature of a seepage behavior monitoring sensing cable reaches a certain value, and observing the temperature reduction degree of the first sensing fiber, the second sensing fiber and the third sensing fiber, thereby determining the monitoring accuracy in different directions;

third, spirally arranging the sensing fibers on second fiber-carrying connecting shafts in four parallel-distributed second fiber-carrying rings in an S-shaped form, then arranging the sensing fibers on a first fiber-carrying connecting shaft on a first fiber-carrying ring and a second fiber-carrying connecting shaft on a second fiber-carrying ring on a right force-bearing beam similarly in an S shape, selecting a fulcrum of a structure to be monitored, placing a dike seepage character space-time monitoring device on the structure to be monitored by a left force-bearing beam and the right force-bearing beam, connecting the sensing fibers in series to a subsequent dike seepage character space-time monitoring device by a first transitional round end at the right force-bearing beam until an area to be monitored is provided with dike seepage character space-time monitoring devices meeting requirements, arranging the sensing fibers that are processed by the sensing fiber seepage-monitoring sensitizing device in the structure to be monitored according to the same path, and performing monitoring and comparison analysis synchronously; and fourth, when seepage water passes through the area to be monitored, optical information of the sensitized sensing fiber in the dike seepage character space-time monitoring device changes continuously, meanwhile, making the unevenly distributed seepage water reach a place around the seepage behavior monitoring sensing cable from different directions, quickly monitoring, by the first sensing fiber, the second sensing fiber and the third sensing fiber, a temperature change brought by the seepage water from different directions by the synergistic effect of at least two sets of seepage isolating enhancement segments and seepage enhancing reinforcement segment, drawing the optical information change of the sensitized sensing fiber in the dike seepage character space-time monitoring device and the seepage behavior monitoring sensing cable according to an arrangement route, drawing curves at different times, and performing comprehensive identification and analysis of the seepage behavior by comparing the respective curves.

Advantageous Effects

The integrated monitoring system for a seepage behavior of water engineering in a complex environment of the present invention has a complete structure and strong flow and automation, integrates a seepage monitoring system embedded with a seepage character space-time monitoring device, a sensing fiber seepage-monitoring sensitizing device and a seepage behavior monitoring sensing cable, implements quantitative and qualitative assessments in the horizontal and longitudinal directions in terms of time and space by providing a series of products and technologies such as research and development in basic sensing fibers and secondary processing of common sensing fibers as well as development of a sensing fiber carrier, has the advantages of intelligence, digitization, integration and miniaturization, implements multi-directional multi-accuracy gradient seepage characteristic identification, and greatly ensures the application and promotion ability of this technology in practical engineering.

Wherein: 100—Vertical connecting shaft; 101—outer fastening ring; 102—left force-bearing beam; 103—first expansion spring; 104—first elastic pipe; 105—first fiber-carrying connecting shaft; 106—first fiber-carrying ring; 107—second fiber-carrying connecting shaft; 108—second fiber-carrying ring; 109—second expansion spring; 110—second elastic pipe; 111—first transitional round end; 112—round plug body; 113—upper and lower bolts; 114—second transitional round end; 115—fiber collecting box; 116—sensing fiber; 117—outer edge through pipe; 118—pointed bottom end; 119—component supporting body; 120—vertical force-bearing fiber-carrying column; 121—right force-bearing beam; 200—first seepage isolating enhancement segment; 201—first sensing fiber; 202—third seepage enhancing reinforcement segment; 203—inner hard four-sided layer; 204—fourth sensing fiber; 205—anti-seepage triangular layer; 206—third seepage isolating enhancement segment; 207—heat-insulating triangular layer; 208—second seepage enhancing reinforcement segment; 209—outer arc filling layer; 210—third sensing fiber; 211—second seepage isolating enhancement segment; 212—second sensing fiber; 213—first seepage enhancing reinforcement segment; 214—inner triangular support; 300—first weight-increasing vertical pull block; 301—tail end transitional wheel; 302—first solid storage pipe; 303—first solid fiber end; 304—upper glue injection pipe; 305—lower glue injection pipe; 306—outer hard layer; 307—outer temperature insulation enhancement layer; 308—outer heat transfer layer; 309—inner heat conduction enhancement layer; 311—inner heat insulation layer; 312—inner super hard layer; 313—upper through pipe; 314—lower through pipe; 315—through pipe handle; 316—glue injection protective plate; 317—glue injection through pipe; 318—through pipe bottom protective seat; 319—second solid fiber end; 320—second solid storage pipe; 321—head end transitional wheel; 322—second weight-increasing vertical pull block.

DETAILED DESCRIPTION OF THE EMBODIMENTS

The present invention will be further described below in conjunction with the accompanying drawings.

Figure 1:
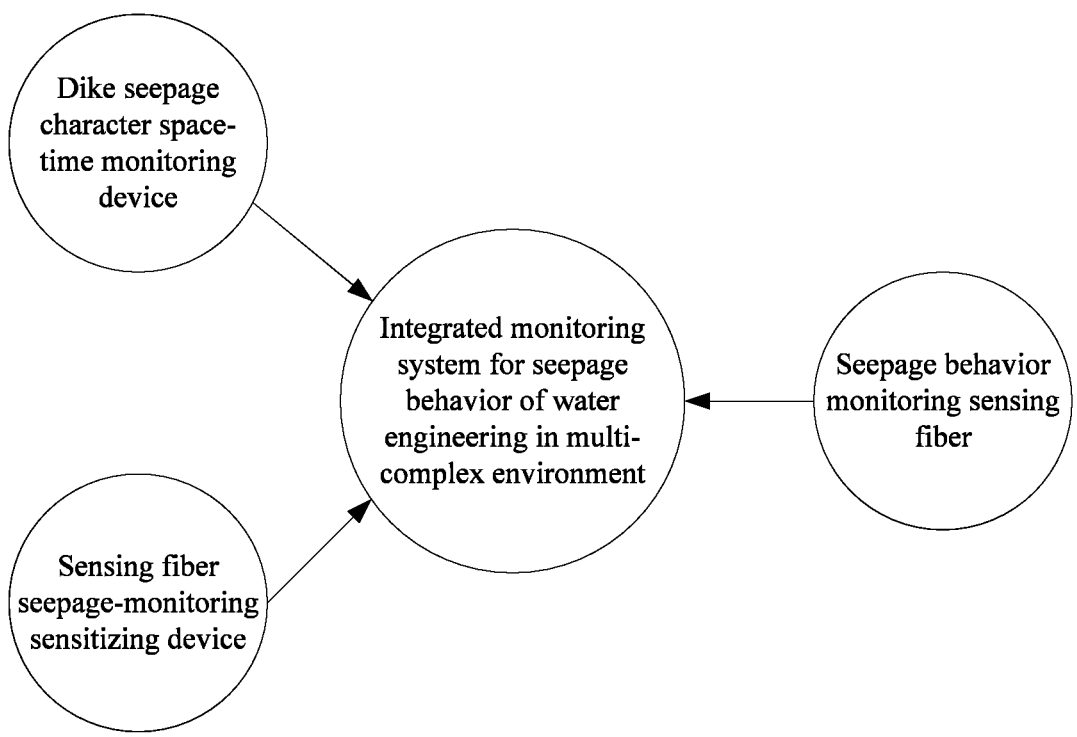
FIG. 1 is a composition diagram of the present invention.
Figure 2:
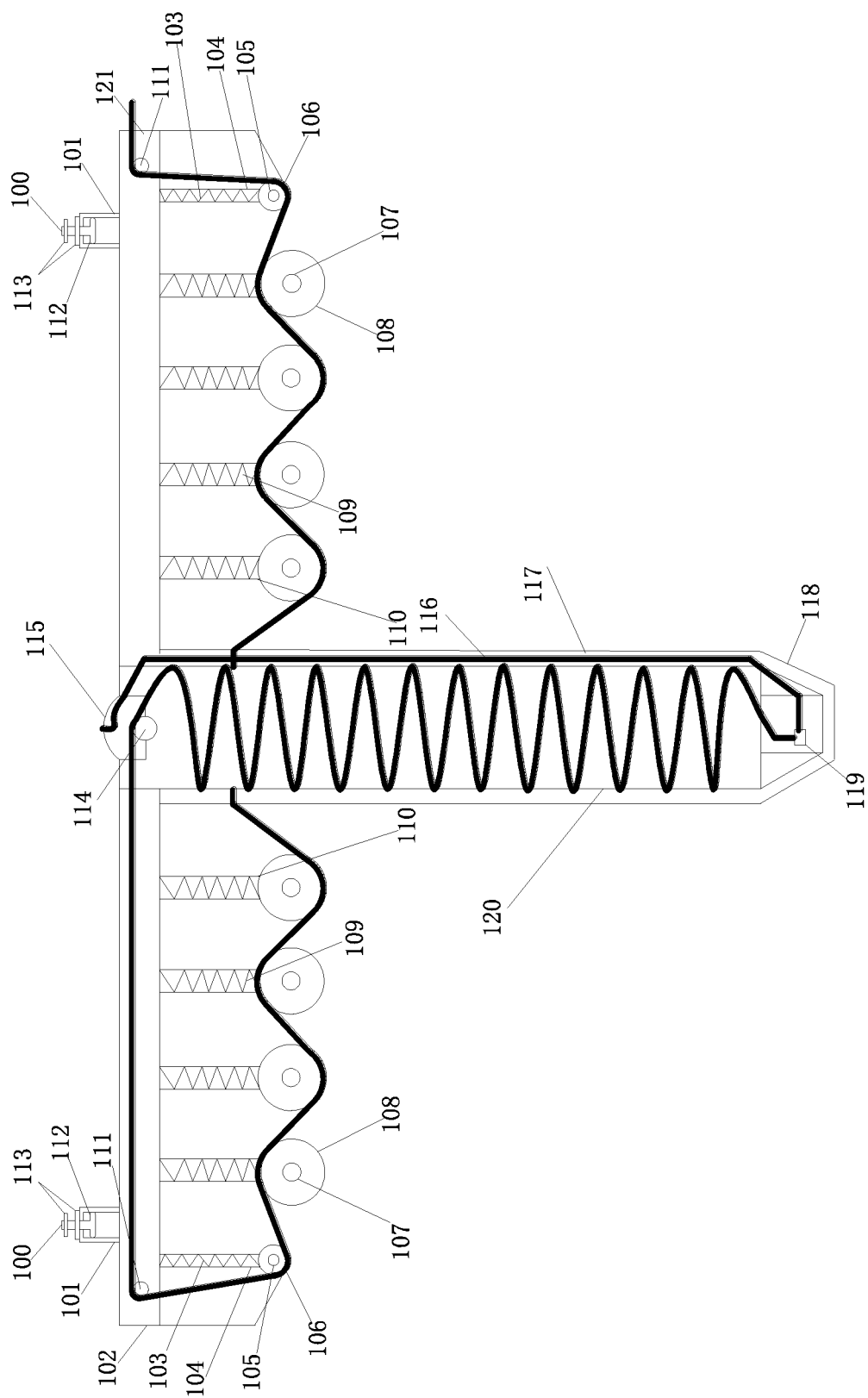
FIG. 2 is a structural diagram of a seepage character space-time monitoring device.
Figure 3:
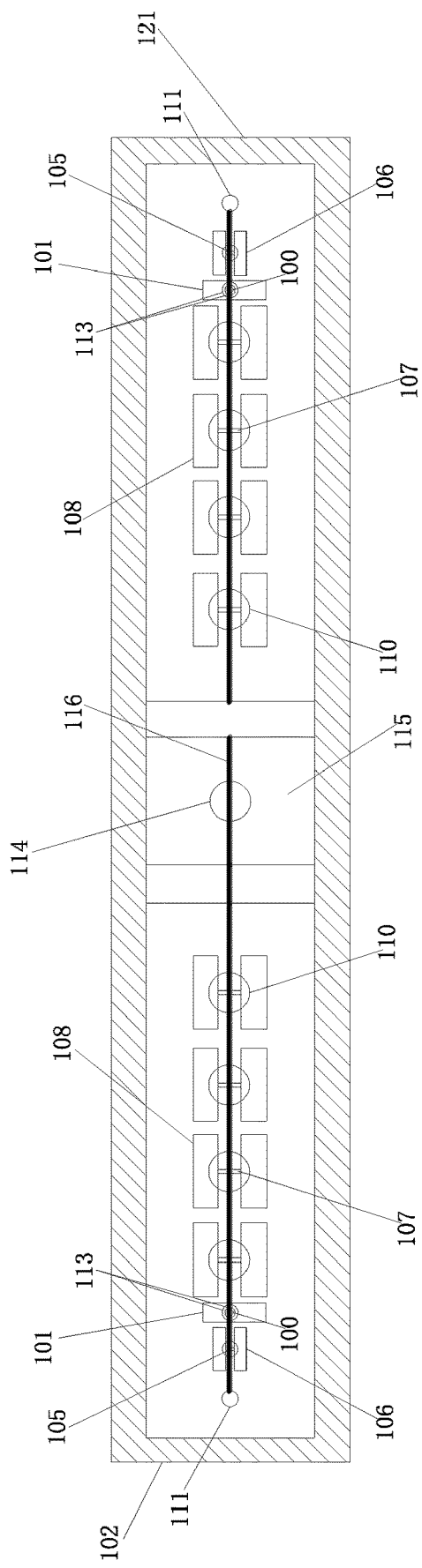
FIG. 3 is a top view of FIG. 2.
Figure 4:
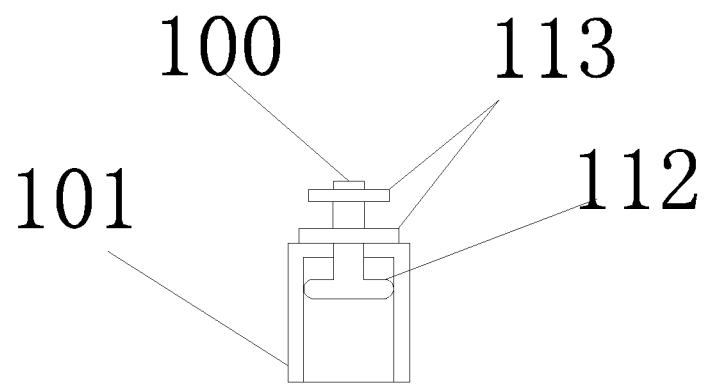
FIG. 4 is a detailed schematic structural diagram of an assembly module in the present invention.
Figure 5:
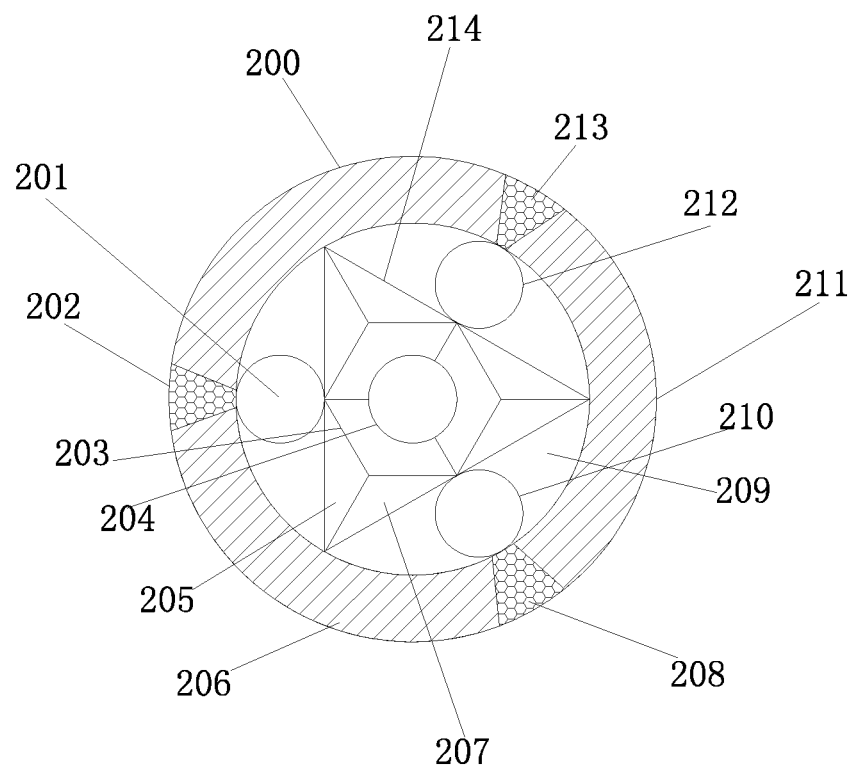
FIG. 5 is a structural diagram of a seepage behavior monitoring sensing cable.
Figure 6:
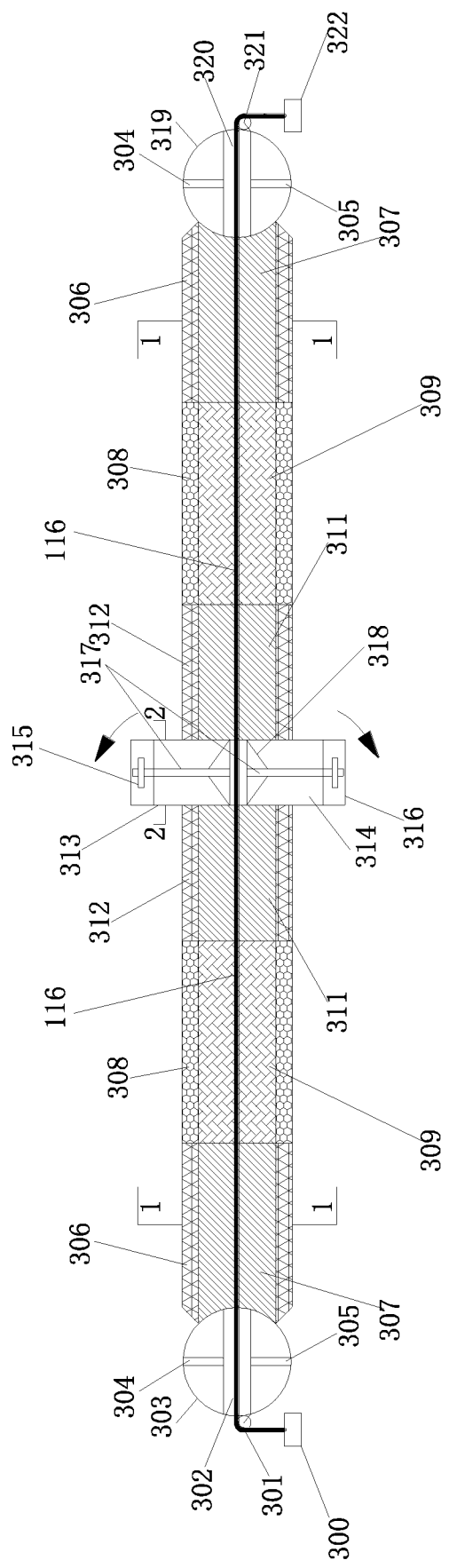
FIG. 6 is a structural diagram of a sensing fiber seepage-monitoring sensitizing device.
Figure 7:
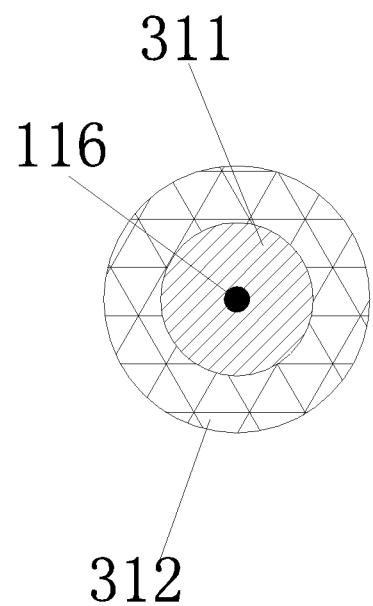
FIG. 7 is a detailed structural diagram of an inner super hard layer and an inner heat insulation layer.
Figure 8:
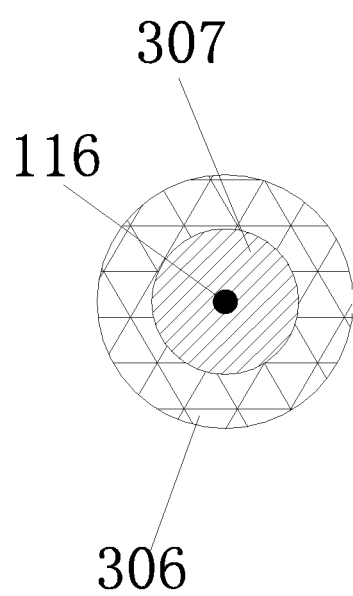
FIG. 8 is a detailed structural diagram of an outer hard layer and an outer temperature insulation enhancement layer in an outer layer module.
Figure 9:
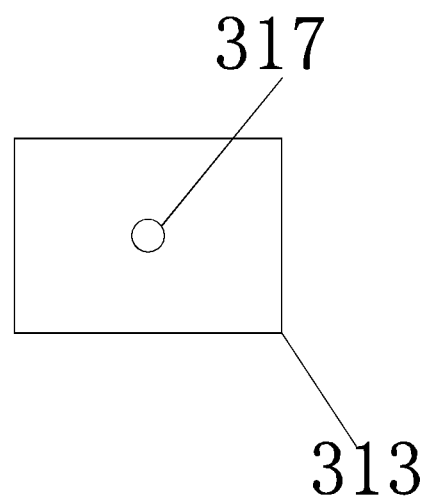
FIG. 9 is a detailed structural diagram of a glue injection through pipe and an upper through pipe in a central control module.

As shown in FIG. 1 to FIG. 9, in this embodiment, a dike section of the Yellow River in water engineering is selected as a seepage area to be monitored, 5 dike seepage character space-time monitoring devices are required for the area, the length of GYTA53+33 type sensing fibers needing to be laid is about 200 m, the length of a seepage behavior monitoring sensing cable needing to be laid is about 210 m, the seepage behavior monitoring sensing cable is disposed in the seepage character space-time monitoring device, and is disposed in the dike area to be monitored together with a sensing fiber seepage-monitoring sensitizing device.

In this embodiment, the seepage character space-time monitoring device includes a horizontal bearing connection module, a vertical frame module and an assembly module, wherein the horizontal bearing connection module is provided with a left force-bearing beam 102 having a length of 50 cm and a right force-bearing beam 121 having a length of 50 cm, the lower bottom ends of the left force-bearing beam 102 having a width of 10 cm and the right force-bearing beam 121 having a width of 10 cm are provided with a first elastic pipe 104 having a diameter of 2 cm and a second elastic pipe 110 having a diameter of 2 cm respectively, and a first transitional round end 111 having a diameter of 3 cm is mounted at each of two outer edge ends of the left force-bearing beam 102 and the right force-bearing beam 121. A first expansion spring 103 having a length of 10 cm and a second expansion spring 109 having a length of 10 cm are mounted in the first elastic pipe 104 and the second elastic pipe 110, the lower bottom end of the first elastic pipe 104 is connected to a first fiber-carrying ring 106 having a diameter of 4 cm, the first fiber-carrying ring 106 having a diameter of 4 cm is internally provided with a first fiber-carrying connecting shaft 105 having a diameter of 2 cm, a second fiber-carrying ring 108 having a diameter of 4 cm is therein provided with a second fiber-carrying connecting shaft 107 having a diameter of 2 cm, and the vertical frame module includes a vertical force-bearing fiber-carrying column 120 having a length of 100 cm and an outer edge through pipe 117 having a length of 100 cm. The seepage behavior monitoring sensing cable is led into the outer edge through pipe 117 having a length of 100 cm through a fiber collecting box 115, the seepage behavior monitoring sensing cable is led into a component supporting body 119 in a pointed bottom end 118 after passing through the pointed bottom end 118 at the bottom end of the outer edge through pipe 117, and a miniature fiber temperature measuring device is mainly placed at the component supporting body 119. The seepage behavior monitoring sensing cable is led into a second transitional round end 114 after passing through the vertical force-bearing fiber-carrying column 120 at the upper end of the pointed bottom end 118, and finally, the seepage behavior monitoring sensing cable is led into the horizontal bearing connection module after passing through the second transitional round end 114 having a diameter of 3 cm. The seepage behavior monitoring sensing cable passes through the first fiber-carrying connecting shaft 105 of the first fiber-carrying ring 106 having a diameter of 4 cm and the second fiber-carrying connecting shaft 107 of the second fiber-carrying ring 108 having a diameter of 4 cm in an S-shaped arrangement form. The seepage behavior monitoring sensing cable passes through the vertical force-bearing fiber-carrying column 120 having a length of 100 cm in a vertical S-shaped arrangement form, and the left force-bearing beam 102 having a width of 10 cm and the right force-bearing beam 121 having a width of 10 cm are vertically connected to the vertical force-bearing fiber-carrying column 120 having a length of 100 cm. The horizontal S-shaped arrangement form for the seepage behavior monitoring sensing cable in the left force-bearing beam 102 and the right force-bearing beam 121 and the longitudinal S-shaped arrangement form for the vertical force-bearing fiber-carrying column 120 having a length of 100 cm constitute a two-way double-S-shaped arrangement structure, and form a horizontal and longitudinal alternate arrangement form. The seepage behavior monitoring sensing cable in the component supporting body 119 is fixed, which will serve as a position mark and a calibration position for the seepage behavior monitoring sensing cable. A vertical connecting shaft 100 in the assembly module is connected to a round plug body 112 through upper and lower bolts 113 arranged in an upper layer and a lower layer, an outer edge of the round plug body 112 is in contact with an inner edge of an outer fastening ring 101, and the assembly module is connected to the horizontal bearing connection module through the outer fastening ring 101.

In this example, the sensing fiber seepage-monitoring sensitizing device includes a central control module, an outer layer module and a port module. A through pipe handle 315 having a diameter of 5 cm is connected to a glue injection through pipe 317 having a diameter of 2 cm and a height of 8 cm. An upper through pipe 313 having a diameter of 5 cm and a height of 10 cm is connected to the glue injection through pipe 317. A glue injection protective plate 316 having a diameter of 5 cm and a height of 1 cm is arranged at the top ends of the upper through pipe 313 having a diameter of 5 cm and a height of 10 cm and a lower through pipe 314 having a diameter of 5 cm and a height of 10 cm. A triangularly conical through pipe bottom protective seat 318 having a height of 2 cm is arranged at the bottom end of the glue injection through pipe 317 having a diameter of 2 cm and a height of 8 cm. The inner side of an inner super hard layer 312 made of a super-high molecular weight polyethylene fiber is connected to the outer side of an inner heat insulation layer 311 made of PET. The inner super hard layer 312 made of a super-high molecular weight polyethylene fiber is adjacent to an inner heat conduction enhancement layer 309 made of a PBT heat conduction material. The outer side of the inner heat conduction enhancement layer 309 made of a PBT heat conduction material is connected to the inner layer of an outer heat transfer layer 308. The inner heat conduction enhancement layer 309 made of a PBT heat conduction material is adjacent to an outer temperature insulation enhancement layer 307 made of a 30% glass fiber reinforced PET material. The outer side of the outer temperature insulation enhancement layer 307 is connected to the inner side of an outer hard layer 306. The outer temperature insulation enhancement layer 307 is adjacent to a spherical first solid fiber end 303 having a diameter of 4 cm. An upper glue injection pipe 304 having a diameter of 2 cm and a height of 1.5 cm is fixed to the upper end sides of the spherical first solid fiber end 303 having a diameter of 4 cm and a spherical second solid fiber end 319 having a diameter of 4 cm. A first solid storage pipe 302 having a length of 4 cm and a diameter of 1 cm is fixed to the middle position between the first solid fiber end 303 and the second solid fiber end 319. A lower glue injection pipe 305 having a diameter of 2 cm and a height of 1.5 cm is fixed to the lower end sides of the first solid fiber end 303 and the second solid fiber end 319. The first solid fiber end 303 is adjacent to a tail end transitional wheel 301. The tail end transitional wheel 301 is adjacent to a rectangular-solid first weight-increasing vertical pull block 300 having a weight of 0.5 kg. The second solid fiber end 319 is adjacent to a head end transitional wheel 321. The head end transitional wheel 321 is adjacent to a second weight-increasing vertical pull block 322.

By rotating the through pipe handle 315 having a diameter of 3 cm, the flow rate of a KJ-770 silica gel bonding agent in the glue injection through pipe 317 having a diameter of 2 cm and a height of 8 cm can be controlled, and the glue injection protective plate 316 having a diameter of 5 cm and a height of 1 cm can protect a top outlet of the glue injection through pipe 317 having a diameter of 2 cm and a height of 8 cm from external interference. The KJ-770 silica gel bonding agent is injected into upper-half sections of the first solid storage pipe 302 and the second solid storage pipe 320 having a length of 4 cm and a diameter of 1 cm by the upper glue injection pipe 304 having a diameter of 2 cm and a height of 1.5 cm. After the KJ-770 silica gel bonding agent at the upper-half sections of the first solid storage pipe 302 and the second solid storage pipe 320 is solidified, the KJ-770 silica gel bonding agent is injected into lower-half section sides of the first solid storage pipe 302 and the second solid storage pipe 320 by the lower glue injection pipe 305 having a diameter of 2 cm and a height of 1.5 cm. A sensing fiber at a head end is straightened by the rectangular-solid second weight-increasing vertical pull block 322 having a weight of 0.5 kg, and then the whole GYTA53+33 type sensing fiber is straightened by the rectangular-solid first weight-increasing vertical pull block 300 having a weight of 0.5 kg, so that the GYTA53+33 type sensing fiber has a certain prestress.

In this example, the seepage behavior monitoring sensing cable includes an outer circle module, a middle layer module and an inner core module. A first seepage isolating enhancement segment 200 having an outer arc length of $\pi/3$ and an inner arc length of $\pi 4/15$ is connected to a second seepage isolating enhancement segment 211 having an outer arc length of $\pi/3$ and an inner arc length of $\pi 4/15$ through a first seepage enhancing reinforcement segment 213 having an outer arc length of $\pi 2/15$ and an inner arc length of $\pi/15$. The second seepage isolating enhancement segment 211 is connected to a third seepage isolating enhancement segment 206 having an outer arc length of $\pi/3$ and an inner arc length of $\pi 4/15$ through a second seepage enhancing reinforcement segment 208 having an outer arc length of $\pi 2/15$ and an inner arc length of $\pi/15$. The third seepage isolating enhancement segment 206 is connected to the first seepage isolating enhancement segment 200 through a third seepage enhancing reinforcement segment 202 having an outer arc length of $\pi 2/15$ and an inner arc length of $\pi/15$. A first sensing fiber 201, a second sensing fiber 212 and a third sensing fiber 210 are connected to each other by an outer arc filling layer 209 made of a super-high molecular weight polyethylene fiber. An inner edge of an inner triangular support 214 having a metal structure is connected to an anti-seepage triangular layer 205 having a vertex angle of 30°. The anti-seepage triangular layer 205 is adjacent to a heat-insulating triangular layer 207 having a vertex angle of 30°. The anti-seepage triangular layer 205 and the heat-insulating triangular layer 207 are used alternately to provide anti-seepage and heat-blocking effects on a fourth sensing fiber 204. The inner edges of the anti-seepage triangular layer 205 and the heat-insulating triangular layer 207 are in contact with an inner hard four-sided layer 203 having a vertex angle of 60° and an inner hard four-sided layer 203 having a vertex angle of 120°. The inner hard four-sided layer 203 mainly functions as an external load buffer. The fourth sensing fiber 204 is mounted at the center surrounded by the inner hard four-sided layer 203. By heating the inner triangular support 214 having a metal structure, the temperature can be increased and reduced manually.

Specific operating steps for an integrated monitoring system for a seepage behavior of water engineering in a complex environment are as follows:

First, prepare a GYTA53+33 type sensing fiber, perform sensitization according to 5 areas needing to be arranged and having a length of 200 m, make a head end of a first section to be sensitized pass through a head end transitional wheel 321 having a diameter of 0.5 cm, a second solid storage pipe 320 having a length of 4 cm and a diameter of 1 cm, a first solid storage pipe 302 having a length of 4 cm and a diameter of 1 cm, and a tail end transitional wheel 301 having a diameter of 0.5 cm, fix a second weight-increasing vertical pull block 322 having a weight of 0.5 kg and a first weight-increasing vertical pull block 300 having a weight of 0.5 kg to two ends of the GYTA53+33 type sensing fiber 310 to realize a single-port load pretensioning force of 5 KN, inject speed glue into the first solid storage pipe 302 and the second solid storage pipe 320 by an upper glue injection pipe 304 and a lower glue injection pipe 305 in a first solid fiber end 303 and a second solid fiber end 319, open through pipe handles 315 at upper and lower ends after the speed glue is solidified to make a KJ-770 silica gel bonding agent flow out from glue injection through pipes 317 at upper and lower sides simultaneously, continuously squeeze the KJ-770 silica gel bonding agent to a gap, in contact with the sensing fiber 310, in an inner heat insulation layer 311, an inner heat conduction enhancement layer 309 and an outer temperature insulation enhancement layer 307 at both sides, encapsulate the sensing fiber 310 at the inner heat insulation layer 311, the inner heat conduction enhancement layer 309 and the outer temperature insulation enhancement layer 307, and after standing for a period of time, perform the similar treatment on parts to be sensitized in the remaining 4 sections.

Second, configure four equal-length common sensing fibers having blue, white, yellow and red tight shielding layers, which sequentially correspond to a first sensing fiber 201, a second sensing fiber 212, a third sensing fiber 210 and a fourth sensing fiber 204, connect a metal inner triangular support 214 using an alternating current, heat the inner triangular support 214, stop heating the inner triangular support 214 after a seepage behavior monitoring sensing cable is heated to a certain extent, wait for half of an hour, then observe the temperature reduction degree of the first sensing fiber 201, the second sensing fiber 212 and the third sensing fiber 210, determine the monitoring accuracy gradient in different directions, and finally complete assembly and debugging of the seepage behavior monitoring sensing cable.

Third, spirally arrange the seepage behavior monitoring sensing cable on second fiber-carrying connecting shafts 107 in four parallel-distributed second fiber-carrying rings 108 in an S-shaped form, then arrange the cable on a first fiber-carrying connecting shaft 105 on a first fiber-carrying ring 106 on a right force-bearing beam 121 and a second fiber-carrying connecting shaft 107 on a second fiber-carrying ring 108 similarly in an S shape, fix a dike seepage character space-time monitoring device to a point A of a dike area to be monitored by an outer fastening ring 101 on a left force-bearing beam 102 and the right force-bearing beam 121, and connect the sensing fibers in series to a subsequent dike seepage character space-time monitoring device by a first transitional round end 111 at the right force-bearing beam 121 until points A, B, C, D and E of the area to be monitored are provided with five dike seepage character space-time monitoring devices meeting requirements.

Fourth, arrange, in parallel, the sensitized GYTA53+33 type sensing fiber along a route through which the five dike seepage character space-time monitoring devices pass according to the layout design of the area to be monitored, so as to realize synchronous monitoring, and perform synchronous monitoring and comparison analysis.

Fifth, perform initial debugging after the above steps are completed, record an initial result, continuously change optical information of the sensitized sensing fiber when seepage water that is not evenly distributed may reach a place around the seepage behavior monitoring sensing cable from different directions, meanwhile, quickly monitor, by the first sensing fiber 201, the second sensing fiber 212 and the third sensing fiber 210, a temperature change brought by the seepage water from different directions by the synergistic effect of a first seepage isolating enhancement segment 200 and a first seepage enhancing reinforcement segment 213, a second seepage isolating enhancement segment 211 and a second seepage enhancing reinforcement segment 208, and a third seepage isolating enhancement segment 206 and a third seepage enhancing reinforcement segment 202, draw the optical information change of the sensitized sensing fiber in the seepage character space-time monitoring device and the seepage behavior monitoring sensing cable according to an arrangement route, draw curves at different times after performing initial value removal with initial monitoring and comparison analysis with the fourth sensing fiber 204, and perform comprehensive identification and analysis of the seepage behavior by comparing the respective curves.

The above description is only a preferred implementation manner of the present invention, and it should be noted that those of ordinary skill in the art can also make several improvements and modifications without departing from the principle of the present invention. These improvements and modifications should be considered as the scope of protection of the present invention.

What is claimed is:

1. An integrated monitoring system for a seepage behavior of water engineering in a complex environment, comprising a seepage character space-time monitoring device and a sensing fiber seepage-monitoring sensitizing device, a sensing fiber being sensitized by the sensing fiber seepage-monitoring sensitizing device, and then the sensing fiber being disposed in the seepage character space-time monitoring device for monitoring; wherein the seepage character space-time monitoring device comprises a vertical force-bearing fiber-carrying column, an outer edge through pipe and a sensing fiber, a left force-bearing beam and a right force-bearing beam are disposed at two sides of the vertical force-bearing fiber-carrying column respectively, the outer edge through pipe is sleeved over the vertical force-bearing fiber-carrying column, the top end of the vertical force-bearing fiber-carrying column is provided with a second transitional round end, the bottom end is provided with a component supporting body, a first transitional round end and a third transitional round end are disposed at both ends of each of the left force-bearing beam and the right force-bearing beam respectively, elastic devices are disposed below the left force-bearing beam and the right force-bearing beam respectively, a fiber collecting box is disposed above the second transitional round end, the sensing fiber in the fiber collecting box runs through the outer edge through pipe to be connected to the component supporting body containing a temperature measuring device, and is then disposed in the vertical force-bearing fiber-carrying column in an S shape, and then runs through the elastic devices below the left force-bearing beam and the right force-bearing beam after sequentially bypassing the second transitional round end and the first transitional round end to be led out from the third transitional round end;

the sensing fiber seepage-monitoring sensitizing device comprises a central control module, outer layer modules and port modules, the outer layer modules and the port modules are disposed at both sides of the central control module, and the outer layer modules are located between the central control module and the port modules;

the central control module comprises a through pipe handle, an upper through pipe, a glue injection through pipe and a lower through pipe, one end of the through pipe handle is connected to the glue injection through pipe, the glue injection through pipe is embedded between the upper through pipe and the lower through pipe, and the sensing fiber is located between the upper through pipe and the lower through pipe;

the outer layer module comprises an inner super hard layer, an inner heat insulation layer, an outer heat transfer layer, an inner heat conduction enhancement layer, an outer hard layer, and an outer temperature insulation enhancement layer, the inner side of the inner super hard layer is connected to the outer side of the inner heat insulation layer, the inner super hard layer is immediately adjacent to the inner heat conduction enhancement layer, the outer side of the inner heat conduction enhancement layer is connected to the inner layer of the outer heat transfer layer, the inner heat conduction enhancement layer is immediately adjacent to the outer temperature insulation enhancement layer, the outer side of the outer temperature insulation enhancement layer is connected to the inner side of the outer hard layer, the outer temperature insulation enhancement layer is immediately adjacent to a solid fiber end, and the sensing fiber sequentially runs through the inner heat insulation layer, the inner heat conduction enhancement layer and the outer temperature insulation enhancement layer; and the port module comprises an upper glue injection pipe, the solid fiber end, a solid storage pipe and a lower glue injection pipe, the upper glue injection pipe is fixed to the upper end side of the solid fiber end, the solid storage pipe is fixed at a middle position of the solid fiber end, the lower glue injection pipe is fixed to the lower end side of the solid fiber end, and the sensing fiber passes through the solid storage pipe.

2. The integrated monitoring system for a seepage behavior of water engineering in a complex environment according to claim 1, wherein the sensing fiber is a seepage behavior monitoring sensing cable, and comprises an outer circle module, a middle layer module and an inner core module, the middle layer module being located between the outer circle module and the inner core module;

the inner core module comprises a fourth sensing fiber and an inner triangular support, the fourth sensing fiber is wrapped with a hard protective layer, a heat insulation protective layer is disposed outside the hard protective layer, the inner triangular support is disposed outside the heat insulation protective layer, and the fourth sensing fiber is located at the center of the inner triangular support;

the middle layer module comprises a first sensing fiber, a second sensing fiber, a third sensing fiber and an outer arc filling layer, the first sensing fiber, the second sensing fiber and the third sensing fiber are located between the inner triangular support and the outer circle module, and the outer arc filling layer is arranged between the inner triangular support and the outer circle module for fixing the first sensing fiber, the second sensing fiber and the third sensing fiber; and the outer circle module is annular, and comprises not less than two sets of seepage isolating enhancement segments and seepage enhancing reinforcement segments, the seepage isolating enhancement segments and the seepage enhancing reinforcement segments are alternately distributed, and the seepage isolating enhancement segments and the seepage enhancing reinforcement segments wrap the first sensing fiber, the second sensing fiber and the third sensing fiber.

3. The integrated monitoring system for a seepage behavior of water engineering in a complex environment according to claim 2, wherein the elastic device comprises a first elastic expansion member and a plurality of second elastic expansion members distributed side by side; the first elastic expansion member comprises a first elastic pipe, a first expansion spring, a first fiber-carrying connecting shaft, and a first fiber-carrying ring connected to the first fiber-carrying connecting shaft, the first expansion spring being located in the first elastic pipe, and the first fiber-carrying connecting shaft being connected to the first expansion spring; and the second elastic expansion member comprises a second elastic pipe, a second expansion spring, a second fiber-carrying connecting shaft, and a second fiber-carrying ring connected to the second fiber-carrying connecting shaft, the second expansion spring being located in the second elastic pipe, the second fiber-carrying connecting shaft being connected to the second expansion spring, and the sensing fiber sequentially running through the first fiber-carrying ring and the second fiber-carrying ring.

4. The integrated monitoring system for a seepage behavior of water engineering in a complex environment according to claim 3, wherein there are four second elastic expansion members, the sensing fiber sequentially runs through the first fiber-carrying ring below the left force-bearing beam, four second fiber-carrying rings below the left force-bearing beam, four second fiber-carrying rings below the right force-bearing beam, and the first fiber-carrying ring below the right force-bearing beam, and the sensing fiber is distributed in an S shape.

5. The integrated monitoring system for a seepage behavior of water engineering in a complex environment according to claim 4, wherein two sides of the central control module are symmetrically provided with the outer layer module and the port module, an end portion of the solid storage pipe is provided with a transitional wheel, and the sensing fiber is connected to a weight-increasing vertical pull block after bypassing the transitional wheel.

6. The integrated monitoring system for a seepage behavior of water engineering in a complex environment according to claim 5, wherein the hard protective layer comprises three inner hard four-sided layers, the inner hard four-sided layer is of a parallelogram with an interior angle of 60°, the fourth sensing fiber is located at the center of the intersection of the three inner hard four-sided layers, and the inner triangular support is of an equilateral triangle.

7. The integrated monitoring system for a seepage behavior of water engineering in a complex environment according to claim 6, wherein the heat insulation protective layer comprises three sets of anti-seepage triangular layers and heat-insulating triangular layers, each set of anti-seepage triangular layer and heat-insulating triangular layer is located at one corner of the inner triangular support, each set of anti-seepage triangular layer and heat-insulating triangular layer is symmetrically distributed about an angle bisector of the inner triangular support, and the anti-seepage triangular layer and the heat-insulating triangular layer are seamlessly connected to the inner hard four-sided layer.

8. A monitoring method of an integrated monitoring system for a seepage behavior of water engineering in a complex environment according to claim 7, comprising the following steps:

first, preparing a common sensing fiber based on actual engineering monitoring needs, determining a length of the sensing fiber to be sensitized, fixing the weight-increasing vertical pull block to a head end of a segment to be sensitized in the sensing fiber, fixing another weight-increasing vertical pull block to a tail end, injecting glue into the solid storage pipe through the upper glue injection pipe and the lower glue injection pipe in the solid fiber end, opening through pipe handles at upper and lower ends to make the glue flow out from glue injection through pipes at upper and lower sides simultaneously, and continuously squeezing the glue to positions, in contact with the sensing fiber, in the inner heat insulation layer, the inner heat conduction enhancement layer and the outer temperature insulation enhancement layer at both sides, so that the inner heat insulation layer, the inner heat conduction enhancement layer and the outer temperature insulation enhancement layer are closely engaged with the sensing fiber, and the sensing fiber at the glue injection through pipe is encapsulated and sealed together by the glue;

second, providing four common sensing fibers with the same length and factory parameters and different colors of tight sheathing layers, sequentially constructing the outer circle module, the middle layer module and the inner core module, then sequentially assembling the inner core module, the middle layer module and the outer circle module in an order from the inside to the outside, recording the colors and corresponding directions of the tight sheathing layers outside the common sensing fibers in different directions, heating an inner triangular support, stop heating after the temperature of the seepage behavior monitoring sensing cable reaches a certain value, and observing the temperature reduction degree of the first sensing fiber, the second sensing fiber and the third sensing fiber, thereby determining the monitoring accuracy in different directions;

third, spirally arranging the sensing fibers on second fiber-carrying connecting shafts in four parallel-distributed second fiber-carrying rings in an S-shaped form, then arranging the sensing fibers on a first fiber-carrying connecting shaft on a first fiber-carrying ring and a second fiber-carrying connecting shaft on a second fiber-carrying ring on a right force-bearing beam similarly in an S shape, selecting a fulcrum of a structure to be monitored, placing the seepage character space-time monitoring device on the structure to be monitored by a left force-bearing beam and the right force-bearing beam, connecting the sensing fibers in series to a subsequent seepage character space-time monitoring device by a first transitional round end at the right force-bearing beam until an area to be monitored is provided with seepage character space-time monitoring devices meeting requirements, arranging the sensing fibers that are processed by the sensing fiber seepage-monitoring sensitizing device in the structure to be monitored according to the same path, and performing monitoring and comparison analysis synchronously; and fourth, when seepage water passes through the area to be monitored, optical information of the sensitized sensing fiber in the seepage character space-time monitoring device changes continuously, meanwhile, the unevenly distributed seepage water reaches a place around the seepage behavior monitoring sensing cable from different directions, quickly monitoring, by the first sensing fiber, the second sensing fiber and the third sensing fiber, a temperature change brought by the seepage water from different directions by the synergistic effect of the at least two sets of seepage isolating enhancement segments and seepage enhancing reinforcement segments, drawing the optical information change of the sensitized sensing fiber in the seepage character space-time monitoring device and the seepage behavior monitoring sensing cable according to an arrangement route, drawing curves at different times, and performing comprehensive identification and analysis of the seepage behavior by comparing the respective curves.

* * * * *